United States Patent [19]

Hansen et al.

[11] Patent Number: 5,075,304

[45] Date of Patent: * Dec. 24, 1991

[54] IMIDAZOQUINOXALINE COMPOUNDS AND THEIR PREPARATION AND USE

[75] Inventors: Holger C. Hansen; Frank Wätjen, both of Vaerlose, Denmark

[73] Assignee: Novo Nordisk A/S, Bagsvaerd, Denmark

[*] Notice: The portion of the term of this patent subsequent to Feb. 20, 2007 has been disclaimed.

[21] Appl. No.: 353,793

[22] Filed: May 18, 1989

[30] Foreign Application Priority Data

Jun. 1, 1988 [DK] Denmark .............................. 2971/88
Nov. 10, 1988 [DK] Denmark .............................. 6259/88

[51] Int. Cl.$^5$ ................. A61K 31/495; A61K 31/535; C07D 487/04
[52] U.S. Cl. ............................... 514/233.2; 514/250; 544/115; 544/346
[58] Field of Search ................ 544/115, 346; 514/234, 514/250

[56] References Cited

U.S. PATENT DOCUMENTS 4,440,929 4/1984 Lee ....................... 544/346
4,774,245 9/1988 Watjen ................. 544/346
4,902,686 2/1990 Watjen ................. 544/346

FOREIGN PATENT DOCUMENTS 320136 6/1989 European Pat. Off. ............ 544/346

Primary Examiner—Mark L. Berch
Attorney, Agent, or Firm—Gordon W. Hueschen

[57] ABSTRACT

New imidazoquinoxaline compounds having the general formula

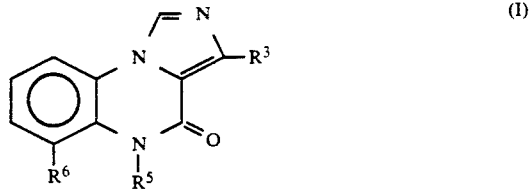

wherein
$R^3$ is

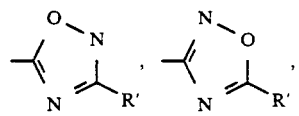

or $CO_2R'$
wherein R' is
  $C_{3-7}$-cycloalkyl;
  $R^5$ is methyl, which is substituted with hydrogen, alkoxycarbonyl, heteroaryl, morpholino, $C_{3-7}$-cycloalkyl, $C_{1-6}$-alkenyl, arylacyl, alkylacyl, alkoxyalkyl, alkoxy, phthalimidophenyl, aralkyl or aryl, all of which are substituted with hydrogen, halogen, $C_{1-6}$-alkyl, amino, azido, or $C_{1-6}$-alkoxy;
  and $R^6$ is H, $C_{1-6}$-alkyl, halogen, or $CF_3$.

The compounds are useful in psychopharmaceutical preparations as anticonvulsants, anxiolytics, hypnotics, and in improving the cognitive function of the brain of mammals.

10 Claims, No Drawings

IMIDAZOQUINOXALINE COMPOUNDS AND THEIR PREPARATION AND USE

The present invention relates to therapeutically active imidazoquinoxaline compounds, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of imidazoquinoxaline compounds have strong affinity for the benzodiazepine receptors which make them useful in psychopharmaceutical preparations.

Accordingly, it is an object of the invention to provide such novel imidazoquinoxaline compounds.

The imidazoquinoxaline compounds of the invention have the general formula I

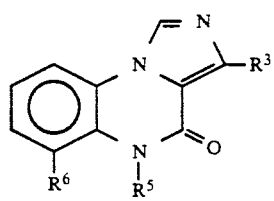

wherein
$R^3$ is

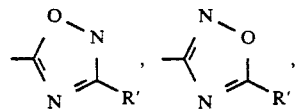

or $CO_2R'$
wherein $R'$ is
$C_{3-7}$-cycloalkyl;
$R^5$ is methyl, which is substituted with hydrogen, alkoxycarbonyl, heteroaryl, morpholino, $C_{3-7}$-cycloalkyl, $C_{1-6}$-alkenyl, arylacyl, alkylacyl, alkoxyalkyl, alkoxy, phthalimidophenyl, aralkyl or aryl, all of which are substituted with hydrogen, halogen, $C_{1-6}$-alkyl, amino, azido, or $C_{1-6}$-alkoxy; and $R^6$ is H, $C_{1-6}$-alkyl, halogen, or $CF_3$.

The invention also relates to a method of preparing the above mentioned compounds. This method comprises:

a) reacting a compound of formula II

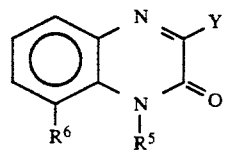

wherein $R^5$ and $R^6$ have the meanings set forth above and wherein Y is a leaving group, with a compound having the formula III $$CN-CH_2-R^3 \qquad (III)$$

wherein $R^3$ has the meaning set forth above, to form a compound of the invention, or b) reacting a reactive derivative of a compound having the general formula IV

wherein $R^5$ and $R^6$ have the meanings set forth above, with a compound having the general formula V $$R'-C(=NOH)NH_2 \qquad (V)$$

wherein $R'$ has the meaning set forth above to form a compound of the general formula I wherein $R^3$ is

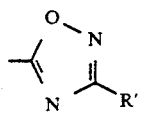

wherein $R'$ has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, $-OP(O)(OR)_2$ wherein R is lower-alkyl or $-OP(O)(NR'R'')$ wherein $R'$ and $R''$ each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available organic compounds and by using well known synthetic methods and as described in Synthesis Vol. 10. pp. 681-682.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of flunitrazepam to benzodiazepine receptors in a living brain to be reduced to 50% of the control value.

Such an in vivo test is carried out as follows:

Principle. Twenty minutes after a dose of $^3$H-flunitrazepam ($^3$H-FNM) (200 μCi/kg, i.v.) the amount of specific $^3$H-FNM binding to brain benzodiazepine receptors has reached its maximal value. This specific binding of $^3$H-FNM can be partly or completely prevented by simultaneous or prior administration of pharmacologically active benzodiazepines and by some benzodiazepine-like agents (Chang and Snyder, Eur.J. Pharmacol. 48, 212–218 (1978)).

Test procedure. Suspensions of test substances (2 mg/ml) are prepared in 5% Duphasol-X (TM Duphar, castor oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 grams) are injected with the test substance at 100 mg/kg intraperitoneally. Fifteen minutes after test substance administration the mice are challenged with 4 μCi intravenously of $^3$H-FNM (70–90 Ci/mole) in 200 μl physiological saline. Twenty minutes after $^3$H-FNM administration mice are sacrificed by decapitation, the forebrains rapidly excised (within 30 sec) and homogenized in 12 ml of ice-cold 25 mM $KH_2PO_4$, pH 7.1, using an Ultra-Turrax homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 μg/kg clonazepam i.p. 30 minutes before $^3$H-FNM to determine the amount of non-specific $^3$H-FNM binding, which should be between 8–15% of total binding. When doses of 100 mg/kg inhibit more than 50% of specific $^3$H-flunitrazepam binding; test substances are administered in doses, which are factors of 3.16 times lower than 100 mg/kg. The $ED_{50}$ for a test substance is defined as that dose which inhibits 50% of specific $^3$H-FNM binding. Specific binding is the amount of binding in controls minus the amount binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25–75%:

$$ED_{50} = (\text{administered dose}) \times \frac{1}{\left[\frac{C_o}{C_x} - 1\right]} \text{ mg/kg}$$

where $C_o$ is specific binding in controls and $C_x$ is specific binding in mice treated with test substance.

Test results obtained by testing some compounds of the invention will appear from the following table I.

TABLE 1

| Compound | $ED_{50}$ (mg/kg) |
|---|---|
| 2 | 0.09 |
| 6 | 0.21 |
| 1 | 1.2 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or more broadly one (1) to thirty (30) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically-acceptable carrier per unit dosage.

A typical tablet which may be prepared by conventional tabletting techniques contains:

| | |
|---|---|
| Active compound | 1.0 mg |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the benzodiazepin receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the socalled benzodiazepin receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1 a. N-phenethyl-2-nitroaniline

To a stirred solution of 1-fluoro-2-nitrobenzene (14.1 g, 0.1 mol) and triethylamine (14 ml, 0.1 mol) in DMF (150 ml) was added phenethylamine (12.1 g, 0.1 mol). The mixture was now heated to 100° C., and the reaction was monitored by TLC. After the reaction was completed (2 h) the solvent was removed by evaporation in vacuo. The residue was partitioned between 0.5N aqueous HCl (100 ml) and ether (100 ml). The organic phase was washed with water, dried and evaporated to give the title compound as a yellow oil.

In a similar manner were prepared the following compounds by reaction between 1-fluoro-2-nitrobenzene and the appropriate amines:

N-(2-morpholinoethyl)-2-nitroaniline. M.p. 42°-44° C.

N-(2-chlorobenzyl)-2-nitroaniline. M.p. 106°-107° C.
N-(2-methoxybenzyl)-2-nitroaniline. M.p. 114°-115° C.
N-(4-methoxybenzyl)-2-nitroaniline. M.p. 92°-93° C.
N-(2-pyridylmethyl)-2-nitroaniline. M.p. 87°-88° C.
N-(2-chlorobenzyl)-2-chloro-6-nitroaniline, m.p. 69°-71° C. was prepared from 2,3-dichloronitrobenzene and 2-chlorobenzyl chloride. Purification on $SiO_2$ (pentane/ether 15:1).

b. N-ethoxalyl-2-nitro-6-methylaniline

To a stirred solution of 2-nitro-6-methylaniline (10 g, 65 mmol) and triethylamine (11 ml, 80 mmol) in THF (80 ml) was dropwise added a solution of ethoxalyl chloride (9 ml, 80 mmol). After completion of the addition the mixture was brought to reflux by external heating. After 3 h the mixture was cooled to room temperature and the precipitated triethylammonium chloride was filtered off. The filtrate was evaporated to give the crude product as an oil. Purification ($SiO_2$/ether:pentane, 1:1) gave the pure title compounds as an oil.

In a similar manner were obtained the following N-ethoxalyl anilines by reaction between ethoxalyl chloride and the corresponding anilines:

N-ethoxalyl-N-(2-methoxybenzyl)-2-nitroaniline. Oil
N-ethoxalyl-N-(4-methoxybenzyl)-2-nitroaniline. Oil
N-ethoxalyl-N-(2-pyridylmethyl)-2-nitroaniline. Oil
N-(2-chlorobenzyl)-N-ethoxalyl-2-nitroaniline. M.p. 98°-99° C.
N-ethoxalyl-N-(2-morpholinoethyl)-2-nitroaniline. M.p. 75°-76° C.
N-benzyl-N-ethoxalyl-2-nitroaniline. M.p. 170°-175° C.
N-(2-chlorobenzyl)-2-chloro-N-ethoxalyl-6-nitroaniline. M.p. 101°-102° C.
N-ethoxalyl-N-phenethyl-2-nitroaniline. Oil
N-cyclopropylmethyl-N-ethoxalyl-2-nitroaniline. Oil c. N-ethoxalyl-N-methyl-2-nitro-6-methylaniline

NaH (1 g, 22 mmol) was added in portions to a stirred solution of N-ethoxalyl-2-nitro-6-methylaniline (5 g, 20 mmol) in DMF (50 ml). Methyl iodide (2 ml, 22 mmol) was thereafter added. The mixture was left overnight at room temperature, whereafter the solvent was removed by evaporation in vacuo. The residue was partitioned between ether and water. The organic phase was washed with water, dried over $Na_2SO_4$ and evaporated to give the title compound as an oil.

In a similar manner was obtained the following compound by alkylation of the appropriate starting materials:

N-ethoxalyl-N-ethyl-2-nitro-6-methylaniline (oil) was prepared from N-ethoxalyl-2-nitro-6-methylaniline and ethyl iodide.

d. N-ethoxalyl-4-chloro-2-trifluoromethylaniline

A mixture of 2-amino-5-chlorobenzotrifluoride (14.4 ml, 0.1 mol) and triethylamine (14.0 ml, 0.1 mol) was dissolved in dry tetrahydrofuran, THF (250 ml). To this solution was added with stirring a solution of ethoxalyl chloride in THF (50 ml). After completion of the addition (30 min.) the mixture was stirred at ambient temperature for 3 h, whereafter the precipitated triethylammonium chloride was filtered off, and the filtrate was evaporated in vacuo. This left the crude title compound (24 g) as pale crystals. M.p. 55°-58° C.

e.
N-ethoxalyl-4-chloro-6-nitro-2-trifluoromethyl-aniline

A solution of N-ethoxalyl-4-chloro-2-trifluoromethylaniline in concentrated sulphuric acid (125 ml) was added to a stirred mixture of 100% nitric acid (120 ml) and concentrated sulphuric acid (240 ml). The temperature was kept between 8°–10° C. during the addition. After the addition was completed, the solution was stirred for additionally 20 min. without external cooling, whereafter it was poured onto icewater. This afforded precipitation of the title compound as an oil, which crystallized as light yellow crystals upon standing. The crystals were filtered off and washed extensively with water. M.p. 100°–101° C.

f.
N-ethoxalyl-N-methyl-4-chloro-6-nitro-2-trifluoromethylaniline

To a stirred solution of N-ethoxalyl-4-chloro-6-nitro-2-trifluoromethylaniline (11 g. 32.3 mmol) and methyl iodide (3.0 ml, 48 mmol) in dry dimethylformamide (DMF, 50 ml) was added in portions sodium hydride (total 1.7 g, 39 mmol). External cooling was used to keep the reaction temperature below 25° C. Stirring was continued at room temperature for 3 h, whereafter the solvent was removed by evaporation in vacuo. The residue was then partitioned between ether and water. The organic phase was washed twice with water, dried over Na$_2$SO$_4$ and evaporated. This treatment left the title compound as an oil, which was processed without further purification.

g.
3,4-dihydro-2-hydroxy-3-oxo-4-methyl-5-trifluoromethylquinoxaline-1-oxide A solution of N-ethoxalyl-N-methyl-4-chloro-6-nitro-2-trifluoroaniline (12 g, 32 mmol) and triethylamine (5.6 ml, 32 mmol) in 96% ethanol (150 ml) was hydrogenated under standard conditions with 5% Pd/C (1 g) as a catalyst. After completion of the reaction, the catalyst was filtered off, and the solvent was removed by evaporation. Treatment of the residue with water/ethyl acetate (150 ml/50 ml) left the product as white crystals, which were collected by filtration. M.p. 196°–198° C.

In a similar manner the following quinoxaline-1-oxides were obtained:
- 4-benzyl-3,4-dihydro-2-hydroxy-3-oxo-quinoxaline-1-oxide, m.p. 170°–175° C. by hydrogenation of N-ethoxalyl-N-benzyl-2-nitroaniline
- 3,4-dihydro-2-hydroxy-4-(2-morpholinoethyl)-3-oxo-quinoxaline-1-oxide. M.p. 170°–172° C. by hydrogenation of N-ethoxalyl-N-(2-morpholinoethyl)-2-nitroaniline
- 3,4-dihydro-2-hydroxy-3-oxo-4-phenethyl-quinoxaline-1-oxide, m.p. 200°–201° C. by hydrogenation of N-ethoxalyl-N-phenethyl-2-nitroaniline
- 4-(2-chlorobenzyl)-3,4-dihydro-2-hydroxy-3-oxo-quinoxaline-1-oxide, m.p. 250°–260° C. decomp. by hydrogenation of N-ethoxalyl-N-(2-chlorobenzyl)-2-nitroaniline. RaNi used as catalyst
- 3,4-dihydro-2-hydroxy-4-(4-methoxybenzyl)-3-oxo-quinoxaline-1-oxide, m.p. 193°–194° C. by hydrogenation of N-ethoxalyl-N-(4-methoxybenzyl)-2-nitroaniline
- 3,4-dihydro-2-hydroxy-4-(2-pyridylmethyl)-3-oxo-quinoxaline-1-oxide, m.p. 220° C. (decomp.) by hydrogenation of N-ethoxalyl-N-(2-pyridylmethyl)-2-nitroaniline
- 3,4-dihydro-2-hydroxy-4-(2-methoxybenzyl)-3-oxo-quinoxaline-1-oxide, m.p. 243°–244° C. by hydrogenation of N-ethoxalyl-N-(2-methoxybenzyl)-2-nitroaniline
- 5-chloro-4-(2-chlorobenzyl)-3,4-dihydro-2-hydroxy-3-oxo-quinoxaline-1-oxide, M.p. 222°–223° C. by hydrogenation of 2-chloro-N-(2-chlorobenzyl)-N-ethoxalyl-6-nitroaniline. RaNi used as catalyst
- 4-cyclopropylmethyl-3,4-dihydro-2-hydroxy-3-oxo-quinoxaline-1-oxide, m.p. 205°–206° C.

In some occasions the hydrogenations did not terminate at the quinoxaline-1-oxide, but at the amino or quinoxaline oxidation state.

h.
4-ethyl-1,2,3,4-tetrahydro-5-methyl-2,3-dioxo-quinoxaline

Hydrogenation of N-ethoxalyl-N-ethyl-6-methyl-2-nitroaniline under standard conditions gave N-ethoxalyl-N-ethyl-2-amino-6-methylaniline as an oil. Ring closure to the title compound was performed in ethanol/1N HCl (50 ml/25 ml) by reflux for 10 min. The product precipitated after cooling and was collected by filtration. M.p.>300° C.

i. 4-benzyl-1,2,3,4-tetrahydro-2,3-dioxo-quinoxaline

A solution of 4-benzyl-1,2,3,4-tetrahydro-2,3-dioxo-quinoxaline-1-oxid (14.6 g, 54 mmol) and triphenylphosphin (21 g, 80 mmol) in dimethylformamide (200 ml) was stirred at 110° C. for 24 h. The solution was evaporated in vacuo, whereafter the residue was stirred in methylene chloride (100 ml). This treatment left the crude title compound as a crystalline precipitate.

The product was purified by recrystallization from ethanol, m.p. 273°–274° C.

In a similar manner the following quinoxalines were prepared from their corresponding 1-oxides:
- 1,2,3,4-tetrahydro-2,3-dioxo-4-phenethyl-quinoxaline, m.p. 105°–106° C.
- 4-(2-chlorobenzyl)-1,2,3,4-tetrahydro-2,3-dioxo-quinoxaline, m.p.>300° C.
- 1,2,3,4-tetrahydro-4-(4-methoxybenzyl)-2,3-dioxo-quinoxaline, m.p. 246°–247° C.
- 5-chloro-4-(2-chlorobenzyl)-1,2,3,4-tetrahydro-2,3-dioxo-quinoxaline, m.p. 234°–236° C.
- 1,2,3,4-tetrahydro-4-(2-methoxybenzyl)-2,3-dioxo-quinoxaline, m.p. 271°–272° C.
- 1,2,3,4-tetrahydro-4-(2-morpholinoethyl)-2,3-dioxo-quinoxaline, m.p. 233°–236° C.
- 1,2,3,4-tetrahydro-4-(2-pyridylmethyl)-2,3-dioxo-quinoxaline, m.p. 295°–297° C.
- 4-cyclopropylmethyl-1,2,3,4-tetrahydro-2,3-dioxo-quinoxaline, m.p. 211°–213° C.

j.
5-benzyl-3-(5-cyclopropyl-1,2,4-oxadiazol-3-yl)-4,5-dihydro-4-oxo-imidazo[1,5-a]quinoxaline (Compound 1)

To an icecooled, stirred solution of 4-benzyl-1,2,3,4-tetrahydro-2,3-dioxo-quinoxaline (1 g, 4 mmol) in dry DMF (20 ml) was added potassium t-butylate (0.56 g, 5 mmol). Stirring was continued until all potassium t-butylate was dissolved. In some experiments a heavy precipitate of the potassium quinoxaline salt was observed.

To the mixture was now added diethyl chlorophosphate (0.7 ml, 5 mmol) and stirring was continued at room temperature for 30 min., whereafter a preformed −40° C. cold solution of potassium t-butylate (0.56 g, 5 mmol) and 5-cyclopropyl-3-isocyanomethyl-1,2,4-oxadiazole (0.8 g, 5 mmol) in dry DMF (15 ml) was added.

The crude product was crystallized from the oily residue by treatment with a mixture of water (25 ml) and ethylacetate (10 ml). The crystals were collected by filtration and purified by column chromatography (SiO₂/ethylacetate), m.p. 250°-255° C.

In a similar manner were prepared the following compounds from the appropriate quinoxalines and isonitriles:

3-(5-cyclopropyl-1,2,4-oxadiazol-3-yl)-4,5-dihydro-5-methyl-4-oxo-6-trifluoromethyl-imidazo[1,5-a]quinoxaline, m.p. 231°-234° C. by reaction between 5-cyclopropyl-3-isocyanomethyl-1,2,4-oxadiazole and 1,2,3,4-tetrahydro-4-methyl-2,3-dioxo-5-trifluoromethyl-quinoxaline (Compound 2)

3-(5-cyclopropyl-1,2,4-oxadiazol-3-yl)-4,5-dihydro-4-oxo-5-phenethyl-imidazo[1,5-a]quinoxaline, m.p. 200°-201° C. by reaction between 5-cyclopropyl-3-isocyanomethyl-1,2,4-oxadiazole and 1,2,3,4-tetrahydro-2,3-dioxo-4-phenethyl-quinoxaline (Compound 3)

5-(2-chlorobenzyl)-3-(5-cyclopropyl-1,2,4-oxadiazol-3-yl)-4,5-dihydro-4-oxo-imidazo[1,5-a]quinoxaline, m.p. 243°-244° C. by reaction between 5-cyclopropyl-3-isocyanomethyl-1,2,4-oxadiazole and 4-(2-chlorobenzyl)-1,2,3,4-tetrahydro-2,3-dioxo-quinoxaline (Compound 4)

3-(5-cyclopropyl-1,2,4-oxadiazol-3-yl)-4,5-dihydro-5-(4-methoxybenzyl)-4-oxo-imidazo[1,5-a]quinoxaline, m.p. 200°-203° C. by reaction between 5-cyclopropyl-3-isocyanomethyl-1,2,4-oxadiazole and 1,2,3,4-tetrahydro-4-(4-methoxybenzyl)-2,3-dioxo-quinoxaline (Compound 5)

3-(3-cyclopropyl-1,2,4-oxadiazol-5-yl)-4,5-dihydro-5-methyl-4-oxo-6-trifluoromethylimidazo[1,5-a]quinoxaline, m.p. 232°-233° C. by reaction between 3-cyclopropyl-5-isocyanomethyl-1,2,4-oxadiazole and 1,2,3,4-tetrahydro-4-methyl-2,3-dioxo-5-trifluoromethyl quinoxaline (Compound 6)

6-chloro-5-(2-chlorobenzyl)-3-(5-cyclopropyl-1,2,4-oxadiazol-3-yl)-4,5-dihydro-4-oxo-imidazo[1 5-a]quinoxaline, m.p. 244°-245° C. by reaction between 5-cyclopropyl-3-isocyanomethyl-1,2,4-oxadiazole and 5-chloro-4-(2-chlorobenzyl)-1,2,3,4-tetrahydro-2,3-dioxo-quinoxaline (Compound 7)

3-(5-cyclopropyl-1,2,4-oxadiazol-3-yl)-4,5-dihydro-4-oxo-5-(2-pyridylmethyl)-imidazo[1,5-a]quinoxaline, m.p. 197°-198° C. by reaction between 5-cyclopropyl-3-isocyanomethyl-1,2,4-oxadiazole and 1,2,3,4-tetrahydro-4-(2-pyridylmethyl)-2,3-dioxo-quinoxaline (Compound 8)

3-(5-cyclopropyl-1,2,4-oxadiazol-3-yl)-4,5-dihydro-5-(2-methoxybenzyl)-4-oxo-imidazo[1,5-a]quinoxaline, m.p. 201°-203° C. by reaction between 5-cyclopropyl-3-isocyanomethyl-1,2,4-oxadiazole and 1,2,3,4-tetrahydro-4-(2-methoxybenzyl)-2,3-dioxo-quinoxaline (Compound 9)

3-(5-cyclopropyl-1,2,4-oxadiazol-3-yl)-4,5-dihydro-5-(2-morpholinoethyl)-4-oxo-imidazo[1,5-a]quinoxaline, m.p. 187°-188° C. by reaction between 5-cyclopropyl-3-isocyanomethyl-1,2,4-oxadiazole and 1,2,3,4-tetrahydro-4-(2-morpholinoethyl)-2,3-dioxo-quinoxaline (Compound 10)

3-(5-cyclopropyl-1,2,4-oxadiazol-3-yl)-5-cyclopropylmethyl-4,5-dihydro-4-oxo-imidazo[1,5-a]quinoxaline, m.p. 213°-215° C. by reaction between 4-cyclopropylmethyl-1,2,3,4-tetrahydro-2,3-dioxo-quinoxaline and 5-cyclopropyl-3-isocyanomethyl-1,2,4-oxadiazole (Compound 11)

Ethyl 4,5-dihydro-5,6-dimethyl-4-oxo-imidazo[1,5-a]quinoxaline-3-carboxylate, m.p. 190°-191° C. by reaction between 1,2,3,4-tetrahydro-4,5-dimethyl-2,3-dioxo-quinoxaline and ethyl isocyanoacetate (Compound 12)

Ethyl 5-ethyl-4,5-dihydro-6-methyl-4-oxo-imidazo[1,5-a]quinoxaline-3-carboxylate, m.p. 159°-160° C. by reaction between 4-ethyl-1,2,3,4-tetrahydro-5-methyl-2,3-dioxo-quinoxaline and ethyl isocyanoacetate (Compound 13)

Ethyl 4,5-dihydro-5-phenethyl-imidazo[1,5-a]quinoxaline-3-carboxylate, m.p. 179°-180° C. by reaction between 1,2,3,4-tetrahydro-2,3-dioxo-4-phenethyl-quinoxaline and ethylisocyanoacetate (Compound 14)

Ethyl 4,5-dihydro-5-(4-methoxybenzyl)-4-oxo-imidazo[1,5-a]-quinoxaline-3-carboxylate, m.p. 194°-195° C. by reaction between 1,2,3,4-tetrahydro-4-(4-methoxybenzyl)-2,3-dioxo-quinoxaline and ethyl isocyanoacetate (Compound 15)

Ethyl 5-(2-chlorobenzyl)-4,5-dihydro-4-oxo-imidazo[1,5-a]-quinoxaline-3-carboxylate, m.p. 203°-209° C. by reaction between 4-(2-chlorobenzyl)-1,2,3,4-tetrahydro-2,3-dioxo-quinoxaline and ethyl isocyanoacetate (Compound 16)

EXAMPLE 2

3-(3-cyclopropyl-1,2,4-oxadiazol-5-yl)-4,5-dihydro-5,6-dimethyl-4-oxo-imidazo[1,5-a]quinoxaline (Compound 17)

A mixture of ethyl 4,5-dihydro-5,6-dimethyl-4-oxo-imidazo[1,5-a]quinoxaline-3-carboxylate (450 mg), cyclopropanecarboxamide oxime (500 mg) and crushed molecular sieves 4 Å (5 g) was charged with a solution of sodium (70 mg) in dry ethanol (50 ml). The stirred mixture was refluxed for 3 h, cooled and filtered through a pad of filter aid. The filtrate was concentrated to a volume of 10 ml by evaporation in vacuo, whereby the title compound partly precipitated. Addition of water (50 ml) afforded an additional precipitation of the title compound. The crystals were collected by filtration and washed with water, m.p. 223°-224° C.

In a similar manner the following oxadiazoles were prepared by reaction between cyclopropanecarboxamide oxime and the corresponding ethyl esters. Purification of the compounds was done by recrystallization from isopropanol.

3-(3-cyclopropyl-1,2,4-oxadiazol-5-yl)-4,5-dihydro-4-oxo-5-phenethyl-imidazo[1,5-a]quinoxaline, m.p. 235°-236° C. (Compound 18)

5-(2-chlorobenzyl)-3-(3-cyclopropyl-1,2,4-oxadiazol-5-yl)-4,5-dihydro-4-oxo-imidazo[1,5-a]quinoxaline, m.p. 276°-277° C. (Compound 19)

3-(3-cyclopropyl-1,2,4-oxadiazol-5-yl)-4,5-dihydro-5-(4-methoxybenzyl)-4-oxo-imidazo[1,5-a]quinoxaline, m.p. 260°-261° C. (Compound 20)

3-(3-cyclopropyl-1,2,4-oxadiazol-5-yl)-5-ethyl-4,5-dihydro-6-methyl-4-oxo-imidazo[1,5-a]quinoxaline, m.p. 211°–212° C. (Compound 21)

EXAMPLE 3

3-(5-cyclopropyl-1,2,4-oxadiazol-3-yl)-5-ethoxycarbonylmethyl-4,5-dihydro-4-oxo-imidazo[1,5-a]quinoxaline (Compound 22)

To a stirred solution of 3-(5-cyclopropyl-1,2,4-oxadiazol-3-yl)-4,5-dihydro-4-oxo-imidazo[1,5-a]quinoxaline (200 mg) in DMF (10 ml) was added sodium hydride (50 mg) and after 10 min ethyl monochloroacetate (1 ml). The mixture was stirred further for 2 h, whereafter the solvent was removed by evaporation in vacuo. The residue was partitioned between water (25 ml) and ether (20 ml), and the crystalline product was filtered off. M.p. 245°–246° C.

With 3-(5-cyclopropyl-1,2,4-oxadiazol-3-yl)-4,5-dihydro-4-oxo-imidazo[1,5-a]quinoxaline and appropriate halides as starting materials and DMF as solvent the following compounds were prepared:

3-(5-cyclopropyl-1,2,4-oxadiazol-3-yl)-4,5-dihydro-5-(3,3-dimethylallyl)-4-oxo-imidazo[1,5-a]quinoxaline, m.p. 133°–134° C. by alkylation with 3,3-dimethylallylbromide. (Compound 23)

5-allyl-3-(5-cyclopropyl-1,2,4-oxadiazol-3-yl)-4 5-dihydro-4-oxo-imidazo[1,5-a]quinoxaline, m.p. 188°–189° C. by alkylation with allylbromide. (Compound 24)

3-(5-cyclopropyl-1,2,4-oxadiazol-3-yl)-4,5-dihydro-4-oxo-5-phenacyl-imidazo[1,5-a]quinoxaline, m.p. 258°–259° C. by alkylation with phenacylbromide (Compound 25)

5-acetonyl-3-(5-cyclopropyl-1,2,4-oxadiazol-3-yl)-4,5-dihydro-4-oxo-imidazo[1,5-a]quinoxaline, m.p. 280°–282° C. by alkylation with chloroacetone. Recrystallization from methanol (Compound 26)

3-(5-cyclopropyl-1,2,4-oxadiazol-3-yl)-5-(2-fluorobenzyl)-4,5-dihydro-4-oxo-imidazo[1,5-a]quinoxaline, m.p. 229°–230° C. by benzylation with 2-fluorobenzylchloride. Recrystallization from toluene (Compound 27)

3-(5-cyclopropyl-1,2,4-oxadiazol-3-yl)-4,5-dihydro-5-(2-methylbenzyl)-4-oxo-imidazo[1,5-a]quinoxaline, m.p. 235°–237° C. by benzylation with 2-methylbenzylchloride. Recrystallization from methanol (Compound 28)

5-(2-bromobenzyl)-3-(5-cyclopropyl-1,2,4-oxadiazol-3-yl)-4,5-dihydro-4-oxo-imidazo[1,5-a]quinoxaline, m.p. 236°–237° C. by benzylation with 2-bromobenzylbromide (Compound 29)

3-(5-cyclopropyl-1,2,4-oxadiazol-3-yl)-4,5-dihydro-5-(3-methoxybenzyl)-4-oxo-imidazo[1,5-a]quinoxaline, m.p. 188°–190° C. by benzylation with m-methoxybenzylchloride, Recrystallization from toluene (Compound 30)

3-(5-cyclopropyl-1,2,4-oxadiazol-3-yl)-5-(2-ethoxyethyl)-4,5-dihydro-4-oxo-imidazo[1,5-a]quinoxaline, m.p. 161°–162° C. by alkylation with 2-bromoethylethyether. Recrystallization from ethanol (Compound 31)

3-(5-cyclopropyl-1,2,4-oxadiazol-3-yl)-4,5-dihydro-4-oxo-5-(4-phthalimidobenzyl)-imidazo[1,5-a]quinoxaline, m.p. 195°–197° C., transition to crystals with m.p. 280°–282° C. by benzylation with 4-(phthalimido)benzyl chloride. Recrystallization from dichloromethane-acetone, 4:1 (Compound 32)

EXAMPLE 4

5-(4-aminobenzyl)-3-(5-cyclopropyl-1,2,4-oxadiazol-3-yl)-4,5-dihydro-4-oxo-imidazo[1,5-a]quinoxaline (Compound 33)

A mixture of 3-(5-cyclopropyl-1,2,4-oxadiazol-3-yl)-4,5-dihydro-4-oxo-5-(4-phthalimidobenzyl)-imidazo[1,5-a]quinoxaline (0.46 g, 0.87 mmol) and hydrazine (2 ml) in ethanol (25 ml) was stirred at room temperature for 1.5 h. The precipitate was collected by filtration, washed with ethanol and dried to give the title compound, m.p. 246°–248° C.

EXAMPLE 5

5-(4-azidobenzyl)-3-(5-cyclopropyl-1,2,4-oxadiazol-3-yl)-4,5-dihydro-4-oxo-imidazo[1,5-a]quinoxaline (Compound 34)

To a stirred solution of 5-(4-aminobenzyl)-3-(5-cyclopropyl-1,2,4-oxadiazol-3-yl)-4,5-dihydro-4-oxo-imidazo[1,5-a]quinoxaline (0.1 g, 0.25 mmol) in trifluoroacetic acid (3 ml) at 0° C. was added sodium nitrite (0.1 g, 1.4 mmol). After 5 min. sodium azide (0.16 g, 2.5 mmol) was added. Stirring was continued for 1 h. Then water (20 ml) was added, and the mixture was extracted twice with dichloromethane (20 ml). The combined extracts were dried over sodium sulphate and evaporated to give the title compound as a pale yellow solid, m.p. 183°–184° C. (dec.). Chromatographic purification ($SiO_2$)/$CH_2Cl_2$-acetone 4:1) gave crystals with m.p. 194°–197° C. (dec.).

What is claimed is:

1. Imidazoquinoxaline compounds having the formula I

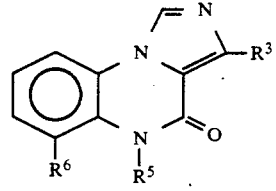

(I)

wherein
R$^3$ is

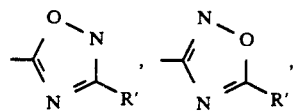

or $CO_2R'$
wherein R' is
   $C_{3-7}$-cycloalkyl;
   R$^5$ is methyl, which may be unsubstituted when R$^6$ is $CF_3$ and which is otherwise substituted with alkoxycarbonyl, pyridyl, morpholino, $C_{3-7}$-cycloalkyl, $C_{1-6}$-alkenyl, aryl carboxylic acyl, alkyl carboxylic acyl, alkoxyalkyl, alkoxy, phthalimidophenyl, aralkyl or aryl, all of which are optionally substituted with halogen, $C_{1-6}$-alkyl, amino, azido, or $C_{1-6}$-alkoxy;
and R$^6$ is H, $C_{1-6}$-alkyl, halogen, or $CF_3$.

2. A compound of claim 1 which is 5-benzyl-3-(5-cyclopropyl-1,2,4-oxadiazol-3-yl)-4,5-dihydro-4-oxo-imidazo[1,5-a]quinoxaline.

3. A compound of claim 1 which is 3-(5-cyclopropyl-1,2,4-oxadiaxol-3-yl)-4,5-dihydro-5-methyl-4-oxo-6-trifluoromethylimidazo[1,5-a]quinoxaline.

4. A compound of claim 1 which is 5-cyclopropylmethyl-3-(5-cyclopropyl-1,2,4-oxadiazol-3-yl)-4,5-dihydro-4-oxo-imidazo[1,5-a]quinoxaline.

5. A compound of claim 1 which is 3-(5-cyclopropyl-1,2,4-oxadiazol-3-yl)-4,5-dihydro-5-(3,3-dimethylallyl)-4-oxo-imidazo[1,5-a]quinoxaline.

6. A compound of claim 1 which is 3-(5-cyclopropyl-1,2,4-oxadiazol-3-yl)-4,5-dihydro-5-(4-methoxybenzyl)-4-oxo-imidazo[1,5-a]quinoxaline.

7. A pharmaceutical composition suitable for use in the treatment of a central nervous system ailment selected from convulsions and anxiety comprising an amount of a compound of claim 1 which is effective for the alleviation of such disorder together with a pharmaceutically-acceptable carrier or diluent.

8. A pharmaceutical composition according to claim 7 wherein it is in the form of an oral dosage unit containing 1-100 mg of the active compound.

9. A method of treating a central nervous system ailment selected from convulsions and anxiety in a subject in need of such treatment comprising the step of administering to said subject an amount of a compound of claim 1 which is effective for the alleviation of such ailment.

10. A method of treating a central nervous system ailment selected from convulsions and anxiety in a subject in need of such treatment comprising the step of administering to said subject an amount of a compound of claim 1 which is effective for the alleviation of such ailment in the form of a pharmaceutical composition thereof, in which it is present together with a pharmaceutically acceptable carrier or diluent.

* * * * *

UNITED STATES PATENT AND TRADEMARK OFFICE
CERTIFICATE OF CORRECTION

PATENT NO. : 5,075,304

DATED : Dec. 24, 1991

INVENTOR(S) : Holger C. Hansen, Frank Wätjen

It is certified that error appears in the above-identified patent and that said Letters Patent is hereby corrected as shown below:

Title Page, [57] ABSTRACT, 2nd formula;

Reads 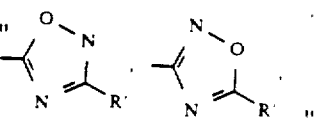 should read 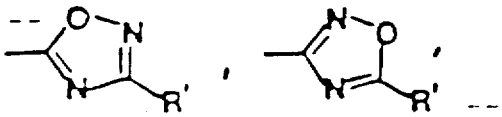

Column 1, line 44;
Reads 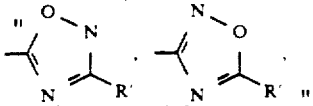 should read 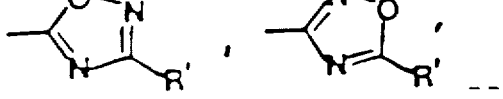

Column 9, lines 45,46; move the closing parenthesis from the beginning of line 46 and insert at the end of line 45 after "6".

Column 9, lines 48/49; "[1, 5-a]" should read --[1,5-1]--.

Column 11, line 27, "-4  5-" should read -- -4,5- --.

Column 12, approximately line 54;

Reads 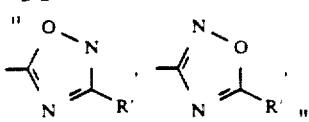 should read 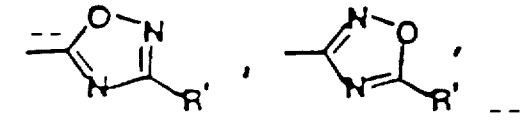

Signed and Sealed this

Fourth Day of May, 1993

Attest:

MICHAEL K. KIRK

Attesting Officer

Acting Commissioner of Patents and Trademarks

UNITED STATES PATENT AND TRADEMARK OFFICE
CERTIFICATE OF CORRECTION

PATENT NO. : 5,075,304
DATED : December 24, 1991
INVENTOR(S) : Holger C. Hansen, et. al.

It is certified that error appears in the above-indentified patent and that said Letters Patent is hereby corrected as shown below:

Title Page, [57] ABSTRACT, 2nd formula;
   Reads 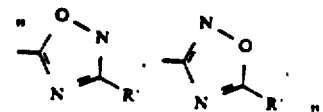 should read 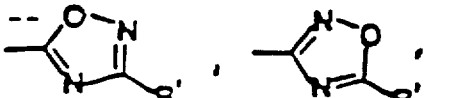

Column 1, line 44;
   Reads 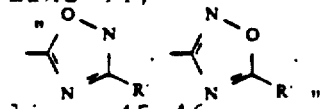 should read 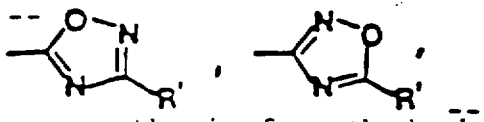

Column 9, lines 45,46; move the closing parenthesis from the beginning of line 46 and insert at the end of line 45 after "6".
Column 9, lines 48/49; "[1  5-a]" should read -- [1,5-a] --.
Column 11, line 27, "-4    5-" should read -- -4,5- --.
Column 12, approximately line 54;
   Reads 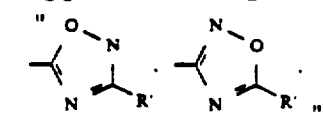 should read 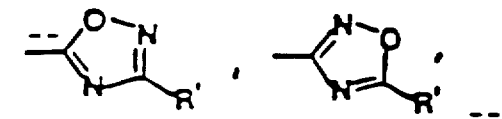

This certificate supercedes Certificate of Correction issued May 4, 1993

Signed and Sealed this

Seventeenth Day of August, 1993

*Attest:*

BRUCE LEHMAN

*Attesting Officer*   *Commissioner of Patents and Trademarks*